United States Patent
Motomura et al.

(10) Patent No.: US 9,129,370 B2
(45) Date of Patent: Sep. 8, 2015

(54) MEDICAL DIAGNOSTIC IMAGING APPARATUS AND IMAGE CORRECTION METHOD

(75) Inventors: Nobutoku Motomura, Nasushiobara (JP); Yasunobu Yamada, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 882 days.

(21) Appl. No.: 12/704,924

(22) Filed: Feb. 12, 2010

(65) Prior Publication Data

US 2010/0202676 A1 Aug. 12, 2010

(30) Foreign Application Priority Data

Feb. 10, 2009 (JP) ................................. 2009-028763

(51) Int. Cl.
*G06T 7/00* (2006.01)
*A61B 6/03* (2006.01)

(52) U.S. Cl.
CPC ............... *G06T 7/0028* (2013.01); *A61B 6/037* (2013.01); *G06T 2207/10081* (2013.01); *G06T 2207/10104* (2013.01); *G06T 2207/10108* (2013.01); *G06T 2207/30056* (2013.01)

(58) Field of Classification Search
None
See application file for complete search history.

(56) References Cited

U.S. PATENT DOCUMENTS

| 2003/0004405 | A1* | 1/2003 | Townsend et al. ............. 600/407 |
| 2003/0233039 | A1* | 12/2003 | Shao et al. .................... 600/407 |
| 2005/0187465 | A1 | 8/2005 | Motomura et al. |
| 2005/0285857 | A1* | 12/2005 | Bonnet et al. ................ 345/420 |

FOREIGN PATENT DOCUMENTS

| CN | 101061520 A | 10/2007 | |
| JP | 2005-106507 | * 1/2005 | ............. G01T 1/161 |
| JP | 2005-106507 | 4/2005 | |
| JP | 2005-195407 | 7/2005 | |
| JP | 2009-25035 | 2/2009 | |
| WO | WO 2007/105536 A1 | 9/2007 | |

OTHER PUBLICATIONS

Certified translation of JP2005-106507 to Honda et al.*
Office Action issued on Aug. 30, 2011 in the corresponding Chinese Patent Application No. 201010116519.8 (with English Translation).
Japanese Office Action issued May 14, 2013, in Japan Patent Application No. 2009-028763 (with English translation).

* cited by examiner

*Primary Examiner* — Mark Holcomb
*Assistant Examiner* — Jason Tiedeman
(74) *Attorney, Agent, or Firm* — Oblon, McClelland, Maier & Neustadt, L.L.P.

(57) ABSTRACT

The CT image processor determines the position of the liver in the body of a subject based on CT image. The PET image processor determines the position of the liver in the body of a subject based on PET image. The CT image processor calculates the displacement in the positions of the liver determined by the CT and PET images. The CT image processor extracts the contour of the liver from a CT image. The CT image processor generates a correction CT image by modifying a CT image by moving a CT image to decrease the displacement of the extracted contour in the internal area. The PET image processor performs decrease correction based on the modified CT image.

10 Claims, 4 Drawing Sheets

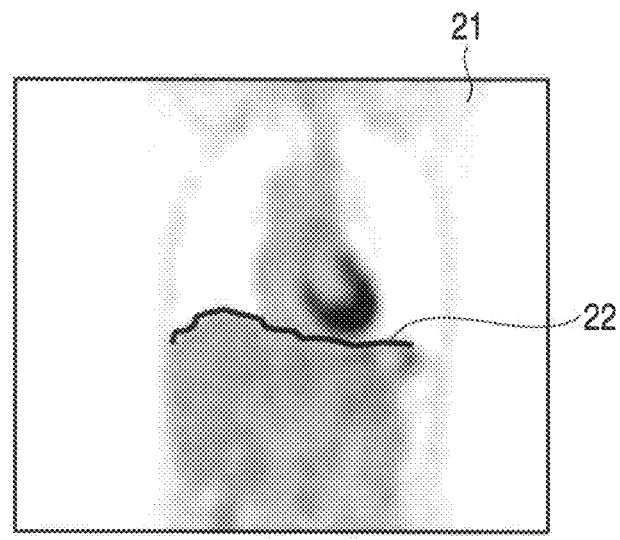
F I G. 3
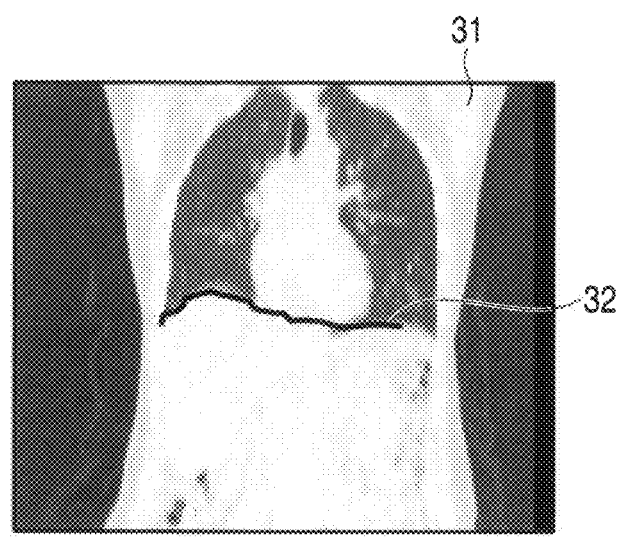
F I G. 4

MEDICAL DIAGNOSTIC IMAGING APPARATUS AND IMAGE CORRECTION METHOD

CROSS-REFERENCE TO RELATED APPLICATIONS

This application is based upon and claims the benefit of priority from prior Japanese Patent Application No. 2009-028763, filed Feb. 10, 2009, the entire contents of which are incorporated herein by reference.

BACKGROUND OF THE INVENTION

1. Field of the Invention

The present invention relates to a nuclear medical diagnostic apparatus such as a gamma camera, single-photon-emission computed tomography (SPECT) scanner or positron emission tomography (PET) scanner, and a composite medical diagnostic imaging apparatus such as a SPECT-CT scanner or PET-CT scanner combining SPECT/PET and X-ray CT (computed tomography).

2. Description of the Related Art

SPECT or PET obtains internal distribution of radioactive tracers given to a subject as a tomographic image. Gamma rays to be measured by SPECT/PET are decreased by Compton scattering and the photoelectric effect in the subject's body. Therefore, correction of the decrease of gamma rays is necessary for correct measurement of the internal distribution of radioactive tracers. This correction is called decrease correction. Decrease correction is a process of correcting a SPECT/PET image to correct the decrease of count value caused by decrease of gamma rays.

Decrease correction needs internal distribution of decrease coefficient of gamma rays. One method of obtaining the distribution of decrease coefficient of gamma rays uses a CT image obtained from the same measuring object. In this method using a CT image, the slice positions of CT and SPECT/PET images must be identical. To obtain the identical slice positions, a SPECT-CT apparatus or a PET-CT apparatus is used to obtain SPECT/PET and CT images. The other method uses different apparatus to obtain CT and XPECT/PET images, and adjusts the positions of the images by using software.

In both methods, the positions of internal organs are inevitably displaced in SPECT/PET and CT images due to different aspiration conditions. It takes long time to obtain a SPECT/PET image, and the position resolution is relatively low. Therefore, a SPECT/PET image is obtained in free aspiration. The time required to obtain a CT is short, and the position resolution is relatively high. Therefore, a CT image is obtained by stopping aspiration. According to the different aspiration conditions, the positions of internal organs are inevitably displaced in SPECT/PET and CT images, even if the same area of a subject is imaged. FIG. 6 shows changes in the positions of the liver according to different aspiration conditions.

The following methods have been taken to solve the above problem:
(1) Obtaining CT and SPECT/PET images in free respiration.
(2) Obtaining CT and SPECT/PET images by stopping respiration (see Jpn. Pat. Appln. KOKAI Publication No. 2005-195407).
(3) Imaging by acquisition in synchronization with respiration.

In all the above methods, CT and SPECT/PET images are obtained in the same respiration condition, and the positions of internal organs are not displaced in both images. However, in method 1, the quality of the CT image is degraded, and the quality of the CT image is unsatisfactory for diagnosis. A SPECT/CT image is complex in method 2, and the time required for imaging is long in method 3.

BRIEF SUMMARY OF THE INVENTION

It is an object of the present invention to provide a medical diagnostic imaging apparatus which can reduce the error of the decrease correction resulting from the disagreement of the position of the internal organs between a CT image and a nuclear medical diagnostic image, acquiring the CT image and the nuclear medical diagnostic image on the suitable conditions for each.

According to an aspect of the present invention, there is provided a medical diagnostic imaging apparatus comprising: a detection unit which detects X-rays passing through a subject; a first regeneration unit which regenerates a CT image of the subject based on the state of the X-rays detected by the detection unit; a measuring unit which measures distribution of radioactive tracers in the subject based on radiation emitted from the radioactive tracers; a second regeneration unit which regenerates a nuclear medical diagnostic image indicating the distribution measured by the measuring unit; a determination unit which determines a predetermined position of an anatomic location in the subject based on the CT image and nuclear medical diagnostic image; a calculation unit which calculates the displacement in the positions determined by the determination unit based on the CT image and nuclear medical diagnostic image; an extraction unit which extracts the contour of the anatomic location from the CT image; a modification unit which modifies the CT image by moving the internal area of the contour extracted by the extraction unit within the CT image so as to decrease the displacement; and a correction unit which corrects the nuclear medical diagnostic image so as to correct the decrease of the radiation based on the CT image corrected by the correction unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a view in which a line indicating the upper edge of the liver is overlaid on a PET image;

FIG. 4 is a view in which a line indicating the upper edge of the liver is overlaid on a CT image;

DETAILED DESCRIPTION OF THE INVENTION

An embodiment of the invention will be explained hereinafter with reference to the accompanying drawings.

Figure 1:
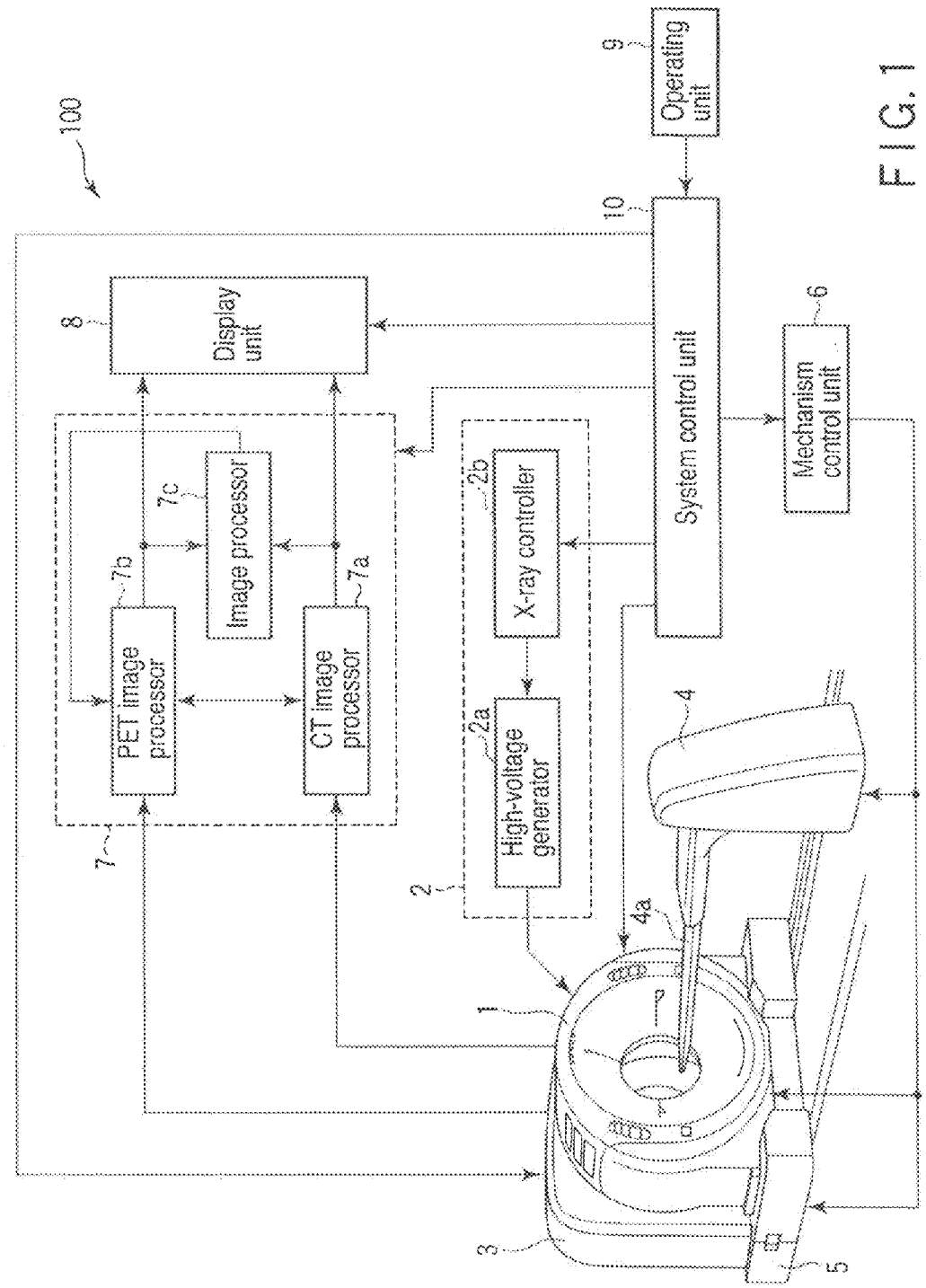
FIG. 1 is a block diagram of a medical diagnostic imaging apparatus according to an embodiment of the invention.

FIG. 1 is a block diagram of a medical diagnostic imaging apparatus 100 according to an embodiment of the invention. The medical diagnostic imaging apparatus 100 comprises a CT rack 1, a high-voltage generator 2, a PET rack 3, a bed 4, a rack moving mechanism 5, a mechanism control unit 6, an image generator 7, a display unit 8, an operating unit 9, and a system control unit 10.

The CT rack 1 has a known internal structure comprising an X-ray tube, an X-ray detector, a rotating ring, a data acquirer, a rotation mechanism, and a tilting mechanism. The CT rack 1 has a housing having a substantially cylindrical opening (CT opening) at the center. The X-ray tube and X-ray detector are held by the rotating ring in the state opposing each other through the CT opening. The X-ray tube emits X-rays to the X-ray detector. The X-ray detector detects the emitted X-rays, and converts them into an electrical signal. The data acquirer acquires and processes the electrical signal output from the X-ray detector. The rotation mechanism rotates the rotating ring about the center of axle of the CT opening as the axis of rotation. The tilting mechanism changes the axis of rotation of the rotating ring.

The high-voltage generator 2 comprises a high-voltage generator 2a, and an X-ray controller 2b. The high-voltage generator 2a generates a high voltage for application between an anode and a cathode to accelerate a thermal electron generated by the cathode of the X-ray tube. The X-ray controller 2b controls the high-voltage generator 2a to adjust X-ray radiation conditions such as a current, voltage and radiation time in the X-ray tube, according to an instruction signal from the system control unit 10.

The PET rack 3 has a known internal structure including a gamma ray detector and a signal processor. The PET rack 3 has a housing having a substantially cylindrical opening (PET opening) at the center. Two or more gamma ray detectors are arranged on a ring provided on the outer circumference of the PET opening. A gamma detector converts gamma rays emitted from radioactive tracers given to the body of a subject into an optical signal, converts the optical signal into an electrical signal, and outputs the electrical signal. The signal processor processes the electrical signal output from the gamma detector.

The CT rack 1 and PET rack 3 are arranged so that the CT opening and PET opening are aligned.

The bed 4 comprises a top board 4a, and a top board moving mechanism. A subject is laid on the top board 4a. The longitudinal axis of the top board 4a is aligned with the CT opening and PET opening. The cross section of the top board 4 crossing the longitudinal axis is shaped to enter the CT opening and PET opening, while a subject is being laid on the top board. The top board moving mechanism moves up and down the top board 4a.

The rack moving mechanism 5 reciprocates the CT rack 1 and PET rack 3 longitudinally with respect to the top board 4a.

The mechanism control unit 6 controls the operations of the rotation mechanism and tilting mechanism of the CT rack 1, the top board moving mechanism of the bed 4, and the rack moving mechanism 5.

The image generator 7 comprises a CT image processor 7a, a PET image processor 7b, and an image processor 7c.

The CT image processor 7a processes the data acquired by the data acquirer of the CT rack 1, and regenerates a CT image. The CT image processor 7a has a function of generating a CT image (correction CT image) used for decrease correction.

The PET image processor 7b processes the data output from the signal processor of the PET rack 3, and regenerates a PET image. The PET image processor 7b has a function of performing decrease correction for regenerating a PET image based on the correction CT image generated by the CT image processor 7a.

The image processor 7c overlays a PET image generated by the PET image processor 7b on a CT image generated by the CT image processor 7a, and generates a composite image. The composite image is fed back to the PET image processor 7b. The image generator 7 outputs CT and PET images to the display unit 8.

The CT image processor 7a has the following functions for generating a correction CT image. One of the functions determines the position of the liver in the body of a subject based on CT and PET images. Another function calculates the displacement in the positions of the liver determined by the CT and PET images. Still another function extracts the contour of the liver from a CT image. The other function generates a correction CT image by modifying a CT image by moving a CT image to decrease the displacement of the extracted contour in the internal area.

The display unit 8 comprises a liquid crystal or CRT monitor, and displays image data processed by the image generator 7.

The operating unit 9 is an interactive interface comprising input devices such as a keyboard, a track ball, a joystick, or a mouse, a display panel, and various switches. The operating unit inputs data about a subject such as age, sex, body type, inspection area, inspection method, past diagnostic records, imaging location (an object organ); sets imaging conditions such as the tilt of the CT rack 1, the positions of the top board 4a, PET rack 3, and bed 4; and inputs various commands.

The system control unit 10 includes a not-shown CPU and storage circuit. The system control unit 10 has a function of controlling each part, like a conventional apparatus can do, for example, a known function of obtaining CT and PET images.

Next, an explanation will be given of the operation of the medical diagnostic imaging apparatus 100 configured as described above.

The medical diagnostic imaging apparatus 100 is configured to perform the operations that can be performed by a conventional PET/CT apparatus. The medical diagnostic imaging apparatus 100 performs the following characteristic operations, when imaging an area including an anatomic location whose position is changed by respiration of a subject. As the position resolution of PET is about 1 cm, the above anatomic location is greatly changed by respiration. The shape of the above anatomic location is assumed to be unchanged, even if the position is changed by respiration. Further, the above anatomic location is assumed to be a location that can be imaged by PET. Here, the above anatomic location is the liver.

First, a CT image is obtained in the CT rack 1, and a PET image is obtained in the PET rack 3. The priority is not specified in CT and PET imaging. A CT image is obtained by stopping respiration, and a PET image is obtained during free respiration.

Figures 2A, 2B:
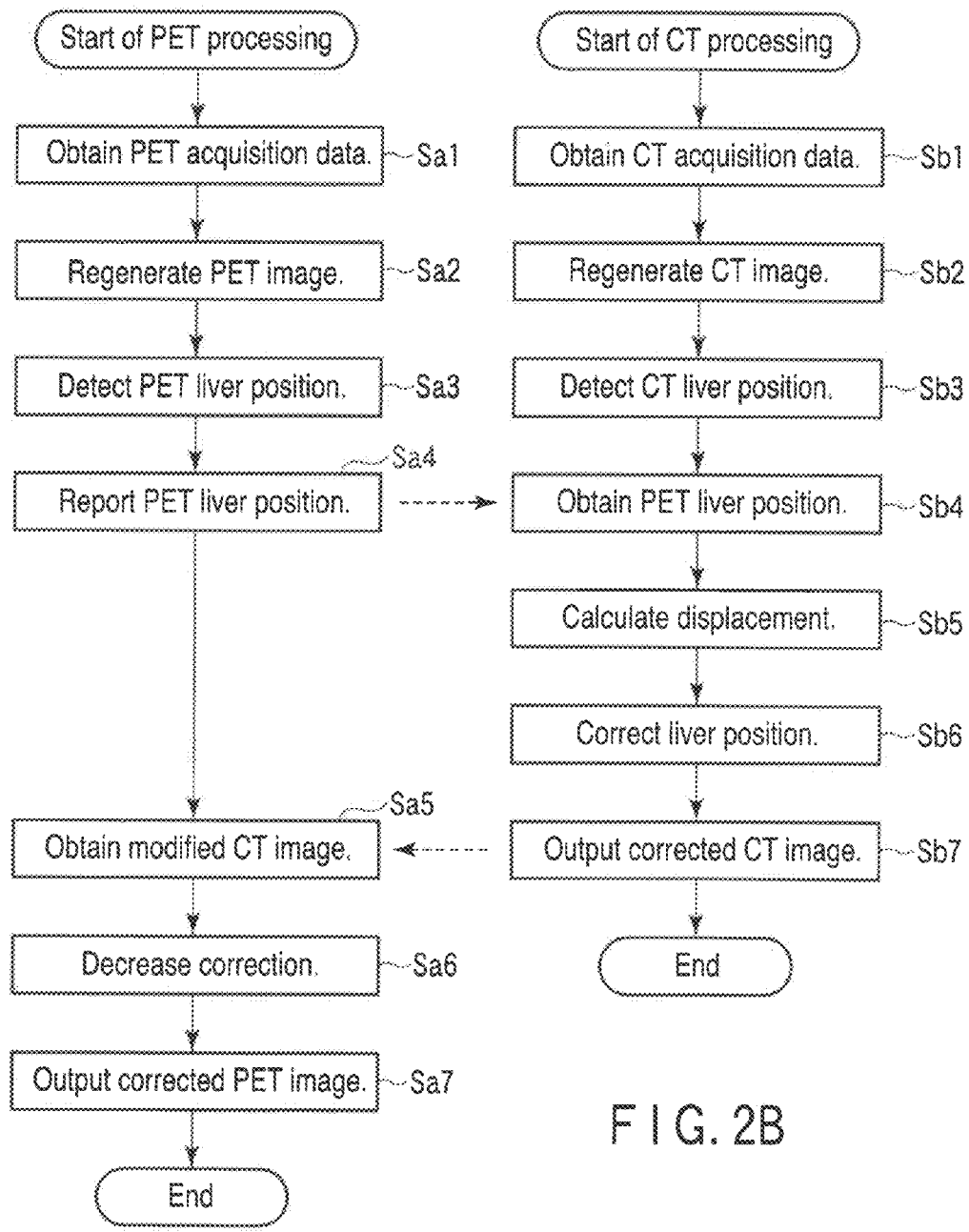
FIG. 2A is a flowchart of processing executed by a PET image processor 7b in FIG. 1.
FIG. 2B is a flowchart of processing executed by a CT image processor 7a in FIG. 1.

FIG. 2A is a flowchart of processing executed by the PET image processor 7b in FIG. 1. FIG. 2B is a flowchart of processing executed by the CT image processor 7a in FIG. 1.

In step Sa1, the PET image processor 7b obtains data acquired from a PET image (PET acquisition data) from the PET rack 3. In step Sa2, the PET image processor 7b regenerates a PET image based on the obtained PET acquisition data. In this regeneration step, decrease correction is not performed.

In step Sa3, the PET image processor 7b detects the position of the liver (PET liver position) based on the regenerated PET image. The PET image processor 7b may automatically detect the liver position from a PET image by using a known method such as a threshold method, or the operator may visually extract the contour of the liver.

FIG. 3 is a view in which a line 22 indicating the upper edge of the liver is overlaid on a PET image 21. A PET liver position is detected as a position of such a line 22, for example. In step Sa4, the PET image processor 7b reports the detected PET liver position to the CT image processor 7a.

In contrast, in step Sb1, the CT image processor 7a obtains data acquired from a CT image (CT acquisition data) from the CT rack 1. In step Sb2, the CT image processor 7a regenerates a CT image based on the obtained CT acquisition data.

In step Sb3, the CT image processor 7a detects the position of the liver (CT liver position) based on the regenerated CT image. The CT image processor 7a may automatically detect the liver position from a CT image by using a known method such as a threshold method, or the operator may visually extract the contour of the liver.

FIG. 4 is a view in which a line 32 indicating the upper edge of the liver is overlaid on a CT image 31. A CT liver position is detected as a position of such a line 32, for example.

Figure 5:
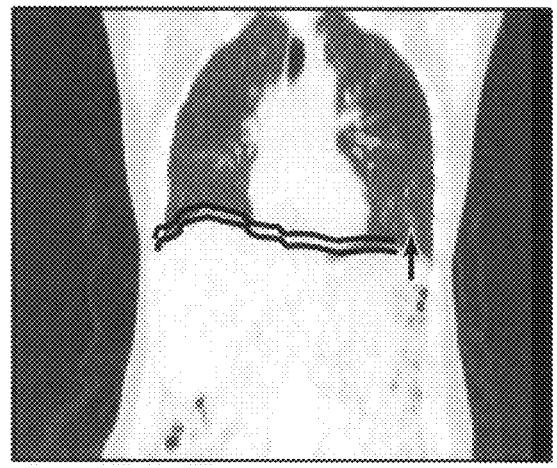
FIG. 5 is a view in which the position of the liver is modified in a CT image.
Figure 6:
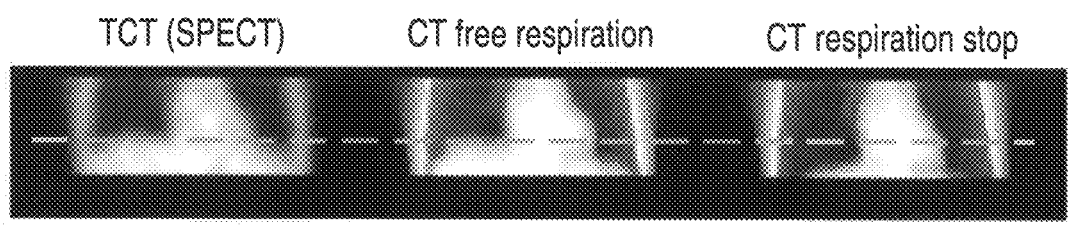
FIG. 6 shows changes in the position of the liver depending on aspiration conditions.

In step Sb4, the CT image processor 7a obtains a PET liver position from the PET image processor 7b, as described above. In step Sb5, the CT image processor 7a calculates the displacement in the CT liver position and PET liver position. In step Sb6, the CT image processor 7a corrects the liver position in the CT image to compensate the calculated displacement. In other words, the CT image processor 7a extracts the liver area in the CT image, and moves the image within the area by the displacement within the CT image. FIG. 5 shows the above correction.

In step Sb7, the CT image processor 7a outputs the modified CT image to the PET image processor 7b, image processor 7c, and display unit 8. The CT image processor 7a thereby completes the processing shown in FIG. 2.

In step Sa4, after reporting the PET liver position to the CT image processor 7a, the PET image processor 7b waits for the output of modified CT image from the CT image processor 7a, and obtains the modified CT image in step Sa5.

In step Sa6, the PET image processor 7b performs decrease correction of the PET image regenerated in step Sa1 based on the modified CT image, or performs decrease correction of the PET acquisition data obtained in step Sa1, and regenerates the PET image based on the corrected data.

In step Sa7, the PET image processor 7b outputs the corrected PET image to the image processor 7c and display unit 8. The PET image processor 7b thereby completes the processing shown in FIG. 2.

According to the embodiment, decrease correction is executed for a PET image based on a CT image in which displacement in the liver position caused by different respiration conditions is corrected. Therefore, a correction error caused by the displacement in the liver position is decreased.

Particularly, in PET or SPECT inspection of the heart (heart PET inspection or heart SPECT inspection), as the heart is close to the liver, displacement in the position of the liver greatly influences the inspection. According to the embodiment described hereinbefore, it is possible to obtain a SPECT/PCT image that is appropriately decrease corrected even in such a case.

The embodiment may be modified in various forms.

The invention may be applicable to cases where SPECT or SPECT/PET is used instead of PET.

The CT rack 1 and PET rack 3 may not be moved, and the bed 4 and top board 4a may be moved. The CT rack 1, PET rack 3, bed 4, and top board 4a may be moved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical diagnostic imaging apparatus comprising:
    a detector configured to detect X-rays passing through a subject; and
    circuitry configured to
        regenerate a computed tomography (CT) image of the subject based on the state of the X-rays detected by the detector;
        measure distribution of radioactive tracers in the subject based on radiation emitted from the radioactive tracers;
        regenerate a nuclear medical diagnostic image indicating the measured distribution;
        determine a plurality of positions of an anatomic landmark structure in the subject using the obtained CT image and nuclear medical diagnostic image respectively, wherein displacement in the plurality of positions are a result of positional changes of the anatomic landmark structure due to respiration;
        calculate the displacement in the determined positions using the CT image and nuclear medical diagnostic image;
        extract a contour of the anatomic landmark structure from the CT image, an internal area of the extracted contour including the anatomic landmark structure;
        decrease the calculated displacement by moving the internal area of the extracted contour within the CT image to generate a modified CT image; and
        correct decrease of the radiation of the nuclear medical diagnostic image based on the modified CT image.

2. The medical diagnostic imaging apparatus according to claim 1, wherein the circuitry is configured to perform decrease correction of the nuclear medical diagnostic image based on the modified CT image.

3. The medical diagnostic imaging apparatus according to claim 1, wherein the anatomic landmark structure is a liver.

4. An image correction method executed by a medical diagnostic imaging apparatus comprising a detector configured to detect X-rays passing through a subject and circuitry, the circuitry being configured to regenerate a computed tomography (CT) image of the subject based on the state of the detected X-rays, measure distribution of radioactive tracers in the subject based on a radiation emitted from the radioactive tracers, and regenerate a nuclear medical diagnostic image indicating the measured distribution, the image correction method comprising:
    determining, using the medical diagnostic imaging apparatus, a plurality of positions of an anatomic landmark structure in the subject using the CT image and nuclear medical diagnostic image respectively obtained by the circuitry, wherein displacement in the plurality of positions are a result of positional changes of the anatomic landmark structure due to respiration;

calculating, using the medical diagnostic imaging apparatus, the displacement in the positions determined in the determining using the CT image and nuclear medical diagnostic image;

extracting, using the medical diagnostic imaging apparatus, a contour of the anatomic landmark structure from the CT image, an internal area of the extracted contour including the anatomic landmark structure;

decreasing, using the medical diagnostic imaging apparatus, the displacement calculated by the calculating by moving the internal area of the contour extracted in the extracting within the CT image to generate a modified CT image; and correcting, using the medical diagnostic imaging apparatus, decrease of the radiation of the nuclear medical diagnostic image based on the modified CT image.

5. The image correction method according to claim 4, wherein the correcting is decrease correction of the nuclear medical diagnostic image based on the modified CT image.

6. The image correction method according to claim 4, wherein the anatomic landmark structure is a liver.

7. The medical diagnostic imaging apparatus according to claim 1, wherein the anatomic landmark structure and an object organ differ from each other.

8. The medical diagnostic imaging apparatus according to claim 7, wherein the object organ is a heart.

9. The image correction method according to claim 4, wherein the anatomic landmark structure and an object organ differ from each other.

10. The image correction method according to claim 9, wherein the object organ is a heart.

* * * * *